United States Patent [19]

Samain et al.

[11] Patent Number: 5,151,264

[45] Date of Patent: Sep. 29, 1992

[54] PARTICULATE VECTOR USEFUL IN PARTICULAR FOR THE TRANSPORT OF MOLECULES WITH BIOLOGICAL ACTIVITY AND PROCESS FOR ITS PREPARATION

[75] Inventors: Daniel Samain, Toulouse; Jean-Louis Bec, Ramonville S. Agne; Edith Cohen, L'Union; Frédérique Nguyen; Marianne Peyrot, both of Toulouse, all of France

[73] Assignee: Centre National de la Recherch Scientifique, Paris, France

[21] Appl. No.: 465,068

[22] PCT Filed: May 11, 1989

[86] PCT No.: PCT/FR89/00229

§ 371 Date: Jan. 26, 1990

§ 102(e) Date: Jan. 26, 1990

[87] PCT Pub. No.: WO89/11271

PCT Pub. Date: Nov. 30, 1989

[30] Foreign Application Priority Data

May 27, 1988 [FR] France ................. 88 07110

[51] Int. Cl.[5] .................. A61K 37/22; A61K 9/14; A61K 9/16; A61K 9/50

[52] U.S. Cl. .................. 424/1.1; 424/408; 424/409; 424/450; 424/489; 424/490; 424/491; 424/492; 424/493; 424/494; 424/495; 424/499; 424/502; 427/213.31; 428/402.24

[58] Field of Search .............. 424/450, 489, 490, 491, 424/492, 493, 494, 495, 499, 502, 408, 409, 1.1; 427/213.31; 428/402.24

[56] References Cited

FOREIGN PATENT DOCUMENTS 0240424 10/1987 European Pat. Off. .
0931150 7/1963 United Kingdom ................. 424/450
2185397 7/1987 United Kingdom .

OTHER PUBLICATIONS

French Search Report and Annex, Application No. 88 07110.
International Search Report and Annex, Application No. FR 8900229.

Primary Examiner—Thurman K. Page
Assistant Examiner—C. Azpuru
Attorney, Agent, or Firm—Cushman, Darby & Cushman

[57] ABSTRACT

A particulate carrier, including a hydrophilic, non-liquid core, a first layer or ring of lipid nature bonded to the core by covalent bonds and a second layer or outer shell of amphiphilic compounds bonded to the first lipid by hydrophobic interactions.

24 Claims, No Drawings

PARTICULATE VECTOR USEFUL IN PARTICULAR FOR THE TRANSPORT OF MOLECULES WITH BIOLOGICAL ACTIVITY AND PROCESS FOR ITS PREPARATION

The present invention relates to a new particulate carrier useable in particular for the transport of molecules having biological activity.

Amongst the processes used to cause a compound (active principle) to penetrate into and react in the interior of a biological or biochemical system it is sometimes valuable to use a particulate carrier in which the active product is encapsulated.

This is the case in particular:

For compounds which in the free state have too short a life time in the body or in the biological or biochemical systems. The carrier then enables the compound to be protected and ensures that it has a constant diffusion.

For compounds which must act on a particular type of cells or must be presented in a certain manner. This is the case for anticancer products and antigens. The carrier can then ensure the presentation and the targeting towards the chosen target.

For compounds which are not naturally absorbed at the level of the mucous membranes: intestine, ENT system, vagina or the skin. The carrier then serves as a coating to facilitate the passage through the barrier.

A particulate carrier of this type must satisfy a certain number of demands relating in particular: to its useful load, its stability, its biometabolization and its possibilities for diffusion of the active principles. In order to be of value it must, in addition, by virtue of its properties, tend to resemble as far as possible natural systems for the transport of molecules in the body or systems encountered in natural media, this being a requirement in order not to disturb the physiological balance and in order to be able to benefit, if appropriate, from the advantages linked to natural vital processes.

Amongst the natural transport systems which the carriers can tend to imitate, the most interesting for study are the lipoproteins.

All of the lipoproteins have the same type of structural organization with an internal lipid core surrounded by phospholipids. An apolipoprotein is furthermore anchored in the phospholipid layer and ensures guiding of the lipoprotein. There are various types of lipoproteins which differ in respect of their size, the nature of the transported lipids and the structure of the apolipoprotein. The chylomicrons, for example, are relatively large lipoproteins (1 $\mu$m) and have the role of transporting the fats arising from digestion. The low density lipoproteins or LDL are much smaller (20-25 nm) and have the role of transporting cholesterol. The small size of the LDL enables them to diffuse within tissues.

The synthetic carrier closest to these natural carriers is a liposome, which consists of a phospholipid bilayer surrounding an aqueous vacuole. The liposomes have been the subject of numerous studies to develop their use as carriers for active principles.

However, they have a number of disadvantages which have prevented their use in the pharmaceutical industry. These are, in particular, their fragility, heterogeneity, their low transport capacity and the difficulties posed by their production on an industrial scale.

It is therefore desirable to have available a carrier which is structurally close to the natural carriers but does not have the drawbacks encountered with liposomes.

The invention in question relates to particulate carriers of a phospholipid/glycolipid/polysaccharide nature, which are also termed Bio Vecteurs Supra Molé culaires (BVSM) [Supramolecular Biocarriers], which permit the transport of molecules of natural, synthetic, semisynthetic or recombinant origin in various biological and biochemical systems: eukaryotes or prokaryotes, for enzymatic, chemical or immunological reactions or diagnostic tests or for fermentations.

Although particulate systems for the transport of active substances have already been described, none of these has the particular multilayer structure of the particulate carriers according to the invention which enables entities of defined size to be obtained which are adjustable and very stable and can be lyophilized, sterilized and completely metabolized and have a structure and surface which are very similar to those of natural carriers More particularly, the present invention relates to a particulate carrier characterized in that it comprises:

a hydrophilic, non-liquid core, essentially a cross-linked hydrophilic polymer, polysaccharide for example, a first layer or ring of lipid nature, generally bonded to the core by covalent bonds, and a second layer or shell of amphiphilic compounds, for example phospholipids, biocompatible detergents or surfactants capable of organizing in micelles, this layer in general being stabilized on the first by hydrophobic interactions.

The hydrophilic core, in particular polysaccharide core, can be obtained by various methods, in particular, in the case of a polysaccharide, a biodegradable polysaccharide will preferably be used which is straight-chain or branched, for example natural or synthetic polysaccharides of the dextran, starch or cellulose type or derivatives of these compounds, in particular derivatives carrying positive or negative ionic charges.

The molecular weight of these polysaccharides can vary very widely from 50,000 to several (almost 10) million daltons. The processes for crosslinking polysaccharides are known in the state of the art and can be carried out by using bifunctional reagents capable of reacting with the hydroxyl functions of sugars; the agents concerned are in particular epichlorohydrin, epibromohydrin, bis-epoxides, mixed anhydrides of dicarboxylic acids or phosphorus oxychloride ($POCl_3$).

The particular parameters for carrying out this type of process are known to those skilled in the art. In general a gel is obtained. This gel must be ground mechanically in order to obtain particles a few tens of microns in diameter. It is then necessary, in order to obtain the carriers according to the present invention, to carry out a fresh fragmentation, which can be carried out by ultrasonic methods or by methods such as extrusion in a French press.

For the particulate carriers according to the present invention it is preferred to use cores having a size of 10 nm to 5 $\mu$m, although in certain cases particles having larger or smaller sizes could possibly be used; the preferred particles are particles having a size of between 20 and 70 nm and preferably of around 50 nm.

The properties of the hydrophilic polysaccharide cores can be modified by introducing ionic, acid or basic functions as substituents into the sugars of the core. This substitution, which takes place in a homogeneous manner inside and on the outside of the core can be introduced before, during or after crosslinking. These ionic properties are of particular value in the case of the encapsulation of compounds which are themselves ionic but of opposite charge to that of the core.

It will be understood that in certain cases, when it is desired to have ranges of homogeneous size, it could be necessary to carry out a purification, as a function of the diameters of the particles obtained, by any appropriate method, in particular by differential centrifuging.

The first layer or ring is preferably obtained by chemical coupling starting from hydroxyl functions or hydroxyl function derived from the core using lipid reactants, that is to say in particular sterols, fatty acids, fatty amines, phospholipids, hydrophobic amino acids or alkoxy ethers.

This type of grafting is known in the state of the art and consists in using reactions for the modification of the hydroxyl functions in sugars in an aprotic medium which is a non-solvent for polysaccharides, such as dichloromethane, hexane or toluene, and the coupling of the hydrophobic radical of the corresponding lipid compound.

Regarding the synthesis of the first lipid layer, while the grafting reactions are effectively known to those skilled in the art, the process according to the invention nevertheless contributes an advantageous modification in a preferred embodiment by carrying out the reaction in an aprotic medium which is a non-solvent for polysaccharides, such as dichloromethane, hexane or toluene. In fact, this enables a derivative formation to be effected on the surface and not in the bulk of the core as would be the case with a solvent for polysaccharides, such as pyridine. This modification is very important since it enables, on the one hand, a central hydrophilic core to be preserved and, on the other hand, the particulate structure of the core to be maintained. In fact, this structure is obtained by virtue of the crosslinking reaction between the hydroxyl functions of the sugars and also by virtue of the presence of hydrogen bonds between the sugars which are not bridged by the crosslinking agent. These bonds are destroyed when derivative formation is effected in the bulk using a solvent for polysaccharides, such as pyridine, and it has been shown that the particulate structure would be lost at the same time (a fiber structure of the cellulose acetate type is then obtained).

To promote the encapsulation of ionic compounds in the first lipid layer it has been found that it was possible to produce lipid rings possessing an underlying ionic character. This ionic character can be conferred by a regioselective reaction of the polysaccharide core with compounds carrying a positive or negative ionic function and another function capable of forming a covalent bond with the hydroxyl functions of the sugars of the polysaccharide core. This is the case, for example, with internal anhydrides of a dicarboxylic acid, such as succinic anhydride, which react with an OH function carried by an alcohol or a sugar to give a monoester of succinic acid possessing a free carboxyl function. The reaction for derivative formation with the ionic compounds can be carried out prior to the acylation reaction with the fatty acids or at the same time. It has been found that the presence of ionic groups on the surface of the polysaccharide core enabled parallel grafting of fatty acid. However, to preserve the hydrophobic character necessary to establish the phospholipid layer, it has been found that this ionic character must not predominate (<40 mol % for succinic acid) and that the fatty acids used must be sufficiently long (>C14). The grafting is conveniently effected by carrying out the reaction for derivative formation in an aprotic medium which is a nonsolvent for polysaccharides, as mentioned above, to ensure the regioselectivity but using a mixture of reactants, one lipid and the other ionic.

Finally, the external lipid shell can be produced with phospholipids or with any ionic or nonionic surfactant capable of organizing in micelles, as has been stated above. This external shell is preferably obtained by methods analogous to those which serve for the preparation of liposomes, that is to say injection of ether or ethanol, dialysis of detergents, reversed-phase preparation or the flask method, which is the best known.

These particulate vehicles are intended more particularly to transport a molecule having biological activity in one of the layers or cores.

Amongst these molecules having biological activity, the following must be mentioned:
  antibiotics and antiviral agents,
  proteins, proteoglycans and peptides,
  polysaccharides and lipopolysaccharides,
  antibodies,
  insecticides and fungicides,
  compounds acting on the cardiovascular system,
  anti-cancer agents,
  anti-malarial agents and
  anti-asthmatic agents.

There are no limitations a priori on the choice of the molecule transported. Virtually all molecules possessing a biological activity can be encapsulated. Many other compounds, for example anti-inflammatory agents, anesthetics, contraceptives, peptides, anti-parasitic agents, vitamins, prostaglandins, neuroleptic agents, antidepressants, and the like, can be added.

In certain cases it is possible to use particulate carriers according to the invention which are uniquely labeled, in particular by radioactive methods or by methods of the fluorescence type or NMR detection type, this labeling being in order to permit imaging and/or diagnosis.

The active principles can be inserted either inside the polysaccharide core or in the lipid ring or in the external phospholipid shell. This insertion can be effected either spontaneously via hydrophobic, hydrogen or ionic bonds or after chemical grafting of an appropriate ligand. In this latter case, the molecules can be localized on the outside of the particle and bonded to the latter by a hydrophobic ligand. Thus, four spatially defined zones are distinguished. It is this division in spatial zones which has led to the adoption of the term Supramolecular.

Finally, the invention relates to pharmaceutical or diagnostic or imaging compositions containing a particulate carrier according to the invention.

In the examples below, the loading of various products as a function of their characteristics will be described, and in particular the loading:
  of a hydrophilic product of small size, an antibiotic of the aminoglycoside family, butirosin,
  of an amphiphilic product, propranolol, localized in the inner lipid ring possessing an acid character,
  of the same propranolol, but this time localized in the external phospholipid shell, of a highly hydrophobic compound, an insecticidal antibiotic, deltamethrin, localized in the inner lipid layer, of a membrane protein, cytochrome C, of a hydrophilic compound of large size but possessing a lipid residue, the lipopolysaccharide of Salmonella minnesota, S form, of an enzymatic protein modified by fatty acid chains, of a monoclonal antibody modified by fatty acid chains, of a hydrophobic antibiotic, erythromycin, of a natural enzymatic protein, peroxidase anchored to the surface of BVSM, of the same peroxidase encapsulated inside an acid polysaccharide core.

The particulate vehicles according to the present invention can be sterilized, in particular by filtration or by treatment in an autoclave at 120° C. for 20 minutes for example. They can be frozen without particular precautions. The lyophilization can be effected in the presence of a lyophilization additive such as maltose, although this is not indispensable, in order to permit rehydration. They can also be atomized. The presence of a sugar or of a polysaccharide in the suspension to be atomized enables the particles to be coated with an glycoside skin which contributes to avoiding the phenomena of agregation between the particles and to permitting better resuspension in water. The examples below permit some of the processes employed in order to insert the products in the different layers of the particulate carriers under consideration to be demonstrated more clearly.

In addition to their significant degree of variability, the BVSM have interesting physicochemical characteristics.

Amongst the numerous advantages of this type of nanoparticles, the following may be mentioned in particular:

the type of modular construction in multilayers allowing adaptation to the product to be transported, to its degree of encapsulation required and to the chosen target, the possibility of modifying the state of the particle surface to promote its reactivity or its intestinal and cutaneous absorption, in a manner similar to liposomes, the external phospholipid shell of the BVSM resembles the cell membrane and is capable of interacting with the latter, a very high chemical stability due to the polymer structure of the polysaccharide core, complete biodegradability and biometabolization, a significant encapsulation capacity for active products of diverse chemical nature, a defined size and the possibility of obtaining very small sizes (50 nm) in a homogeneous manner, enabling control of the diffusion in the biological systems and tissues, the possibility of scaling up the manufacturing process to an industrial scale.

The examples below permit better demonstration of other characteristics and advantages of the present invention.

EXAMPLE 1

Preparation of Crosslinked Polysaccharide Cores 150 g of dextran with a molecular weight of 229,000 is mixed with 150 ml of a 1M sodium hydroxide solution in a 2 liter reactor fitted with a sodium hydroxide trap. When the dextran solution is homogeneous, 12 ml of epichlorohydrin are poured in, while stirring vigorously. The reaction mixture is heated to 80° C. with the aid of a water bath. Stirring is stopped after the addition of the epichlorohydrin, while the temperature is kept at 80° C. for 10 hours.

A slightly elastic and brittle gel is obtained. This gel is suspended in 1.850 l of water and the suspension is then ground mechanically using a screw apparatus (Waring type blender) in order to obtain particles several tens of microns in diameter.

An ultrafragmentation of the crosslinked dextran is then carried out to obtain nanoparticles 50 nm in size. The fragmentation can be carried out by any method which is sufficiently vigorous to permit nanogrinding. The two following methods are given by way of example.

a) Ultrafragmentation by ultrasound

The crude suspension previously obtained is treated with sound for 30 minutes using an ultrasonic probe (power 250 watts). A heterogeneous mixture containing 20% of particles having a diameter smaller than 100 nm is obtained.

b) Fragmentation with a French press

The crude suspension previously obtained is extruded using a French press under an actual pressure of 140 Mpascal. This operation is repeated 3 times. The proportion of particles having a diameter greater than 100 nm is then less than 5%. The average diameter determined by electron microscopy is 50 nm.

The nanoparticles are purified by differential centrifuging at between 1000 g and 6000 g (15 min). The particles sedimenting below 2000 g have a size greater than 100 nm, while those sedimenting at between 2000 and 5000 g have a size of between 10 and 100 nm. These values are variable and depend on the crosslinking conditions and on the nature of the polysaccharides employed.

The size of the particles is measured by electron microscopy (20,000 and 100,000 times magnification) and with a Coulter nanosizer. The particles are in the form of relatively regular spheroids.

90% of the starting polysaccharide is found in the crosslinked insoluble form, while 10% is found in the soluble polysaccharide form. The determination is carried out using the anthrone method. The dehydration of the crosslinked polysaccharide particles is effected using a Büchi 190 atomizer. The concentration of the particles is 5% and the temperature of the drying air is 200° C.

Preparation of acid crosslinked polysaccharide cores 50 g of polysaccharide cores obtained previously by polymerization and fragmentation are dispersed in 1 l of distilled water and the pH is adjusted to 8 with NaOH. 20 g of succinic anhydride are added and the suspension is stirred for 2 hours at room temperature. The modified nanoparticles are then centrifuged and washed to remove the soluble reaction products and the salts. This reaction leads to the formation of succinic acid monoester.

Preparation of alkaline crosslinked polysaccharide cores 50 g of polysaccharide cores are dispersed as before in 1 l of distilled water. The pH is adjusted to 8 and 20 g of glycidyltrimethylammonium chloride are added. The suspension is stirred for 24 hours at room temperature. The modified nanoparticles are centrifuged and washed to remove the soluble reaction products and the salts. This reaction leads to grafting of 1-trimethylamino, 2-ol-1-propyloxy groups on the sugars.

The degree of substitution is approximately 0.5 equivalent per sugar, determined by titration. As a result of the repulsion which exists between the ionic functions of the same charge, the ionic substituents are distributed in a homogeneous fashion in the volume of the particle.

EXAMPLE 2

Preparation of the Lipid Ring with a Lipid Character According to Example 1

75 g of dimethylaminopyridine and 100 g of octanoyl chloride are added to 100 g of atomized polysaccharide particles having an average diameter of 50 nm suspended in 1 l of dichloromethane. The whole is stirred, shielded from air, at 37° C. for 20 hours. The recovery and the washing of the particles after reaction is effected by evaporation of the dichloromethane followed by three washings with methanol. After each washing, the particles are recovered by centrifuging (20 min at 5000 rpm).

Study of the reaction kinetics enables a lipid layer which is dense to a greater or lesser degree and is established at a greater or lesser depth inside the particle to be obtained as a function of the stoichiometry of the components, the solvent used and the temperature chosen.

Example of variation in the degree of grafting of fatty acid as a function of the operating conditions for particles having a diameter of 50 nm.

| Ratio of weight of particles/weight of of octanoyl chloride | Temperature °C. | Reaction time (hours) | Degree of grafting (% by weight) |
| --- | --- | --- | --- |
| 1 | 37 | 18 | 5 |
| 5 | 37 | 18 | 0.6 |
| 0.5 | 37 | 5 | 1.5 |

The fatty acids grafted on the polysaccharide core were determined by the Lauwerys method.

EXAMPLE 3

Preparation of the Lipid Ring with an Ionic Character

Acid character

The above procedure is modified using a mixture of stearoyl chloride (C18) and succinic anhydride. 75 g of dimethylaminopyridine and 160 g of stearoyl chloride (0.8 equivalent) and 12 g of succinic anhydride (0.2 equivalent) are added to 100 g of atomized polysaccharide particles 50 nm in size suspended in 1 l of dichloromethane. The C18/succinic anhydride molar ratio can be varied and the following degree of grafting is obtained:

| Molar ratio C18/Succinic anhydride | Temperature °C. | Time (hours) | Degree of grafting A.G. % by weight |
| --- | --- | --- | --- |
| 1/0 | 37 | 48 | 10 |
| 0.9/0.1 | 37 | 48 | 9.2 |
| 0.75/0.25 | 37 | 48 | 8 |
| 0.6/0.4 | 37 | 48 | 7 |

Basic character

A similar procedure is used with a mixture of acid chloride/glycidyl trimethylammonium chloride.

EXAMPLE 4

Preparation of the External Lipid Shell 30 g of phospholipids (⅓ phosphatidylethanolamine, ⅓ P. choline, ⅓ P. inositol) in 1.5 l of chloroform are added to 150 g of particles (30–100 nm) acylated with octanoic acid (5% of fatty acid). The whole, introduced into a 5 l flask, is brought to dryness under reduced pressure on a rotary evaporator and then, after adding 2 l of distilled water, is placed at 40° C. for 30 min, stirring every 10 min.

It is possible to use a variant of this method, mixing the acyl cores and the phospholipids in the powder state and then progressively adding the necessary amount of water while stirring. This variant is, of course, more suitable for the preparation of large amounts of BVSM.

The BVSM are then obtained in the form of a homogeneous suspension by sonication (1 h 30 in the bath) or by extrusion in a French press. The liposomes (SUV) which have been able to form in the course of the operation as a result of the presence of an excess of phospholipids are removed by centrifuging (15,000 rpm, 30 min); the BVSM having sedimented out are recovered.

The BVSM resuspended by dispersion for a few minutes in an ultrasonic bath are in the form of a milky solution. This suspension is stable but finally settles after several days; simple stirring in a non-forceful manner then suffices to obtain the starting suspension again.

The determination of the phospholipids is carried out by the determination of the phosphorus by the Ames and Dubin method. In the case of cores having a degree of octanoic acid grafting of 5%, the quantity of phospholipids associated with the BVSM is 15%.

EXAMPLE 5

Sterilization of 50 nm BVSM by Filtration

The sterilization of the BVSM having a diameter smaller than 100 nm is achieved by filtration through cellulose acetate or polycarbonate membranes (pores 0.22 μm in diameter). This filtration necessitates the use of an elevated pressure but does not involve clogging phenomena.

Two successive filtrations are needed to obtain a complete sterilization. After filtration, the suspension obtained is remarkably homogeneous and has an extremely low tendency to sediment out (several weeks), which must reflect the highly dispersed state of the suspension caused by the extrusion effect of the membrane.

The BVSM thus obtained can be treated in an autoclave without particular precautions at 120° C. for 20 minutes. After autoclave treatment, the BVSM suspensions appear unchanged.

The BVSM can also be frozen without particular precautions. After thawing, the suspension obtained is identical to the starting suspension. Direct lyophilization of the BVSM can be carried out, but the addition of a lyophilization additive such as 5% maltose enables better results and a perfect suspension to be obtained after lyophilization and rehydration (see paragraph AED).

EXAMPLE 6

Study of the BVSM

Observation of the BVSM by electron microscopy after negative coloration (magnification 100,000 times) indicates that these BVSM have a more or less regular spheroid form with an average diameter of 40 nm.

The particles are observed in the dispersed state without the presence of aggregates. The presence of a halo around the BVSM particles and absent from the polysaccharide cores alone reveals the presence of the external phospholipid shell.

Differential enthalpy analysis study was carried out on the BVSM surrounded by dipalmitoylphosphatidylcholine (DPPC) and by comparison with DPPC liposomes. In this latter case a transition temperature of 40° C. is observed, which is in agreement with the literature data. Analogous transition temperatures are observed for the BVSM of large size (20–80 $\mu$m) and irrespective of the fatty acid present in the lipid ring: C8-40.9° C., C12-40.2° C., C16-40.7° C. In the case of BVSM 50 nm in size, a transition is observed only for the BVSM acylated with octanoic acid (40° C.). These results indicate that the external lipid shell has an organized architecture of the liposomal type. However, this organization is dependant on the nature of the fatty acids making up the lipid ring and on the size of the particles.

Moreover, the transition temperature is not affected by lyophilization of the BVSM.

EXAMPLE 7

Loading of Butirosin in the BVSM

Butirosin (Parke Davis) is an antibiotic of the aminoglycoside family. It is a molecule consisting of an aminocylitol (sic) bonded by glycoside bonds to amino sugars. It is therefore a highly polar and ionic product which is soluble only in water and mixtures of water and lower alcohols.

Blank BVSM are first prepared from 50 g of C8 acylated polysaccharide cores (0.6% of fatty acid) and 10 g of asolectin (Fluka) by the flask method described above.

After washing the BVSM to remove any contaminant liposomes, the BVSM are taken up in suspension in 250 ml of a methanol/water (50:50) mixture containing 10 g of butirosin sulfate (Parke Davis). The suspension thus obtained is concentrated under reduced pressure (30° C., 30 mmHg) using a rotary evaporator. When the suspension becomes pasty, 250 ml of the methanol/water mixture are added. The operation is then repeated three times. After the final concentration, the residue is taken up in 250 ml of water, the mixture is then centrifuged and the butirosin is determined in the supernatant liquor by ion pair high performance liquid chromatography and by microbiological determination on *Bacillus subtilis*. The results indicate the presence of 3 g of butirosin in the supernatant liquor or, by difference, 7 g in the pellet containing the BVSM. A degree of loading of 14% relative to the weight of acylated cores and an encapsulation yield of 70% are thus obtained. After washing the free butirosin by successive centrifuging, the presence of butirosin cannot be detected by analysis of the supernatant liquor from the suspensions containing the BVSM. This butirosin is therefore encapsulated in a stable manner inside the BVSM.

The butirosin encapsulated in the BVSM is no longer active on *Bacillus subtilis* in a Petri dish.

These results taken together demonstrate that butirosin is localized inside the particles, in the polysaccharide core.

Similar results have been obtained with other aminoglycosides, in particular gentamicin.

EXAMPLE 8

Loading of Propranolol in BVSM a) Loading in the internal lipid ring of acid character Propranolol (ICI Pharma) is a beta-blocker which possesses an amphiphilic structure with a lipophilic aromatic part and a basic ionic part due to the presence of a secondary amine.

A suspension is produced with 50 g of cores acylated with a mixture of palmitoyl chloride and succinic anhydride (75/25) as described above. The cores are dispersed in 500 ml of a methanol/water (50:50) solution. 10 g of basic propranolol are added to this suspension and the solvent is evaporated under reduced pressure (40° C., 30 mmHg) using a rotary evaporator. After complete evaporation, the residue is taken up in 200 ml of the same methanol/water mixture and the suspension is again evaporated. After three evaporation cycles, 10 g of phospholipid (lecithin) in powder form are added to the residue. 500 ml of water are then added in small portions and with regular stirring. The suspension is then homogenized, first using a Waring type blender apparatus and then by sonic treatment or by extruding in the French press. The suspension is centrifuged and the propranolol is determined in the supernatant liquor by measuring the absorption at 290 nm. An amount of 2 g of propranolol is found in the supernatant liquor, or, by difference, 8 g in the BVSM. The encapsulation yield is thus 80% with a degree of loading of loading (sic) of 16%.

b) Loading of propranolol in the external lipid shell

The procedure here is as in the case of butirosin. Blank (C8) BVSM are first prepared, propranolol is then added in a methanol/water (50:50) solution and several concentration cycles are carried out (without going to dryness however). The residue is then resuspended in water, the suspension is homogenized and centrifuged (5000 g, 10 min) and propranolol is determined by UV spectrometry at 290 nm in the supernatant liquor. With the same quantities as above, an encapsulation yield of 30% and a degree of loading of 6% are found, these being values lower by half than the preceding values.

EXAMPLE 9

Loading of Deltamethrin in the BVSM

Deltamethrin (Roussel Uclaf) is an insecticide of the pyrethrinoid family. It is an extremely hydrophobic compound which is soluble only in organic solvents.

Loading is carried out starting from 50 g of C16 cores (8% of grafted fatty acid). These cores are suspended in 500 ml of ethanol containing 5 g of deltamethrin. The solvent is evaporated under reduced pressure (30° C., 30 mmHg) using a rotary evaporator. The residue is taken up in 300 ml of ethanol and the suspension is again evaporated. After three evaporation cycles, 10 g of phospholipids (asolectin) are added to the dry residue and 500 ml of water are added in small portions with constant stirring. The suspension is then homogenized with a Waring blender and using the French press and then centrifuged. Given the insolubility of deltamethrin in aqueous solutions, the determination is not carried out on the supernatant liquor but after extraction of the deltamethrin from the BVSM. After washing several times (water and methanol/water mixture), the suspension is centrifuged (5000 g, 10 min). The supernatant liquor is removed and the pellet containing the BVSM is resuspended in absolute ethanol (500 ml). After stirring for 30 min, the suspension is centrifuged (3000 g, 5 min), the supernatant liquor is recovered and the pellet is resuspended in 500 ml of absolute ethanol. After three extractions, the supernatant liquors are combined and deltamethrin is determined by measuring the optical density at 278 nm.

5 g of deltamethrin are found, corresponding to an encapsulation yield of 100% and a degree of loading of 10%. The very high value of the encapsulation yield is certainly due to the highly hydrophobic character of deltamethrin and to its insolubility in water.

EXAMPLE 10

Loading of Cytochrome C in the BVSM

Cytochrome C is a membrane protein which should therefore possess a good affinity for the lipid regions: internal ring and external shell. To compare the efficacy of the various procedures, we carried out the encapsulation on the acylated cores, on the BVSM and by coupling the two methods.

The procedures employed are the same as those used above. The amounts employed are: 50 g of C8 cores, 10 g of asolectin and 10 g of cytochrome C; the methanol was replaced by acetonitrile, which denatures the proteins less.

Coupling of the two methods

A first encapsulation is carried out on the C8 cores and the BVSM are then prepared by the addition of phospholipids and the usual treatment. At this stage, instead of centrifuging the BVSM and determining cytochrome in the supernatant liquor, acetonitrile is added and two further concentration cycles are carried out under reduced pressure (30° C., 30 mmHg). The residue is then taken up in suspension in water, the suspension is homogenized and centrifuged and cytochrome C is determined in the supernatant liquor by measuring the optical density at 407 nm.

The following results are obtained:

| Procedure | Encapsulation yield (%) | Degree of loading (%) |
|---|---|---|
| Acylated cores | 75 | 15 |
| BVSM 67 | 13.4 | |
| 2 methods coupled | 82 | 16.4 |

The use of the two methods coupled gives the best results.

EXAMPLE 11

Loading of the Lipopolysaccharide (LPS) of Salmonella Minnesota (S) in the BVSM

The LPS is a macromolecule consisting of a polysaccharide (or O-antigen) part and a hydrophobic part, the lipid A. It is a membrane constituent of Gramnegative bacteria usually located on the outside of the bacteria. The localization chosen for the LPS is therefore the phospholipid external shell. The procedure used for gentamicin and propranolol starting from blank BVSM is again employed here.

The blank BVSM are prepared as above; the LPS (L 2137, Sigma) is added to the BVSM in suspension in a methanol/water (30/70) mixture. Three concentration cycles are carried out, the residue is resuspended in water, the suspension is homogenized and centrifuged and the LPS is determined in the supernatant liquor by the Dubois (anthrone) method. Starting from 50 g of C8 cores and 5 g of LPS, the encapsulation of 4 g of LPS is achieved, corresponding to an encapsulation yield of 80% and a degree of loading of 8%.

EXAMPLE 12

Loading of Alpha-Chymotrypsin Modified by Hydrophobic Chains in the BVSM

Preparation of modified alpha-chymotrypsin 50 mg of palmitoyl chloride dissolved in 10 ml of acetone are added to 100 ml of a phosphate buffer ($10^{-3}$M, 0.145M NaCl and 1% of cholate at pH 8). The solution is homogenized using an ultrasonic apparatus. Alpha-chymotrypsin (250 mg) dissolved in 10 ml of buffer is then added. After two hours at 4° C., the precipitate is separated off by centrifuging (1 hour, 20,000 g) and the detergent is dialysed out.

Incorporation of the modified alpha-chymotrypsin in the BVSM

A suspension of blank BVSM is prepared by the usual method starting from 2 g of C8 cores and 400 mg of asolectin, the solution of modified alpha-chymotrypsin obtained previously is added to the suspension of blank BVSM and the mixture is adjusted to an acetonitrile concentration of 10% and then concentrated under reduced pressure (1 mmHg, 4° C.) on a rotary evaporator. The operation is repeated 3 times, the residue is then resuspended in 50 ml of water and the suspension is homogenized and centrifuged.

The determination of the proteins in the BVSM by the Bradford method indicates an amount of 200 mg, corresponding to an encapsulation yield of 80% and a degree of loading of 10%.

EXAMPLE 13

Loading of a Monoclonal Antibody Modified by Fatty Acid Chains in the BVSM

Preparation of the modified antibody

One milligram of purified anti-HLA-B2m complex, SAF1 Class 1 (Biosys) is added to 22 μg of N-hydroxysuccinimide ester of palmitic acid in 500 μl of PBS buffer containing 2% of deoxycholate. The mixture is incubated at 37° C. for 12 hours and then chromatographed on a Sephadex G-75 column in a PBS buffer containing 0.15% of deoxycholate to remove the excess palmitic acid. The void volume peak containing the immunoglobulin is collected and dialysed.

Incorporation of the antibody in the BVSM

A suspension of blank BVSM corresponding to 20 mg of C8 cores in 200 μl of water is used. The antibody solution obtained previously is added and the mixture is made up to an acetonitrile concentration of 10%. The mixture is then concentrated under reduced pressure (without going to dryness) using a Speed Vac type apparatus (4° C., 0.01 mmHg). The mixture is resuspended in 500 μl of an acetonitrile/water (10:90) solution and then concentrated again. After three concentration cycles, the suspension is taken up in 500 μl of water, homogenized and centrifuged. Determination of the proteins in the deposit by the Bradford method indicates the presence of 1 mg of protein, corresponding to approximately 100% encapsulation yield and a degree of loading of 5%.

EXAMPLE 14

Loading of Erythromycin in the BVSM

A suspension is produced with 50 g of C12 acylated cores (5% by weight) in 500 ml of a water/methanol (50:50) mixture. 10 g of erythromycin (Eli Lilly) are added to this suspension and the solvent is evaporated off under reduced pressure (40° C., 30 mmHg) using a rotary evaporator. After complete evaporation, the residue is taken up in 200 ml of the same methanol/water mixture and the suspension is again evaporated.

After three evaporation cycles, 10 g of phospholipids (asolectin) in powder form are added to the residue. The customary method is then followed. The erythromycin is determined in the supernatant liquor by HPLC on a C18 column and detected by UV spectroscopy at 228 nm. No erythromycin is found in the supernatant liquor; all of the product has been encapsulated in the BVSM. The encapsulation yield is thus 100% with a degree of loading of 20%.

EXAMPLE 15

Loading of Peroxidase on the Surface of the BVSM

Peroxidase (Sigma) is an enzyme with a molecular weight of 40,000 daltons and an isoelectric point of 7.2. The objective is to achieve immobilization of the enzyme in a stable manner on the BVSM support without denaturing it.

Neutral BVSM. Polysaccharide particles with a size of between 1 and 3 μm are used. 50 g of these particles acylated with stearoyl chloride are placed in a 500 ml flask and intimately mixed with 5 g of peroxidase and with 5 g of hydrogenated lecithin. 250 ml of distilled water are then added in small portions and with vigorous stirring. The suspension obtained is incubated at 37° C. with vigorous stirring and then sonicated for 1 min in an ultrasonic tank. The BVSM are centrifuged and the peroxidase which has not been encapsulated is determined in the supernatant liquor by measuring the optical density at 402 nm. 250 mg of peroxidase are found in the supernatant liquor, corresponding, by difference, to a degree of encapsulation of 95%.

Acid BVSM. Polysaccharide particles identical to those used above are used. 50 g of these particles acylated by a mixture of stearoyl chloride (0.8 equivalent)-/succinic anhydride (0.2 equivalent) are placed as before in a 500 ml flask and mixed with 5 g of peroxidase and with 5 g of hydrogenated lecithin. After the same treatment as above, the suspension is centrifuged and the peroxidase which has not been encapsulated is determined in the supernatant liquor by measuring the optical density at 402 nm. 375 g are found, corresponding to a degree of encapsulation of 92.5%.

EXAMPLE 16

Loading of Peroxidase in the Acid Polysaccharide Core of the BVSM 10 g of acid polysaccharide cores are prepared according to Example 1 by reacting polysaccharide cores with succinic anhydride. The cores have a diameter of between 1 and 3 microns and possess openings sufficiently large to enable proteins with a molecular weight lower than 50,000 daltons to penetrate into the interior of the openings in the particle. The cores are stirred gently in 100 ml of acetate buffer of pH 5.5 in the presence of 5 g of peroxidase for 24 hours. The particles are then centrifuged and the peroxidase is determined in the supernatant liquor by measuring the optical density at 402 nm. 500 mg are found, corresponding to an encapsulation yield of 90% and a degree of encapsulation of 45%. The particles are washed with distilled water, lyophilized and acylated under the customary conditions with stearoyl chloride. The acylated particles are mixed with 1 g of hydrogenated lecithin and 150 ml of distilled water are added in small portions while stirring. A homogeneous suspension of BVSM is obtained after stirring for 30 min at 37° C. Although the acylation reaction took place only at the periphery of the cores, it is possible that part of the peroxidase has been acetylated (sic) in the course of this reaction.

EXAMPLE 17

Study of the Stability of Products Encapsulated in the BVSM

This study was carried out in detail on the BVSM loaded with propranolol, as described in Example 7. Similar results have also been obtained with the other products.

The leakage of propranolol was evaluated by measuring the optical density at 290 nm of the supernatant liquor from a suspension of acid BVSM loaded with 8.4% of propranolol. The BVSM (500 mg of cores, 42 mg of propranolol) are suspended in 20 ml of water. The analysis of the supernatant liquor indicates the presence of 1.76 mg of free propranolol, corresponding to 4% of the total.

The lyophilization and atomization were carried out with the addition of 5% of maltose (Wt/V) to the suspension of BVSM to be dehydrated.

| Storage time (days) in solution at 4° C. | 0 | 1 | 2 | 3 | 4 |
|---|---|---|---|---|---|
| O.D. | 0.241 | 0.415 | 0.234 | 0.228 | 0.241 |
| % of free propranolol | 4 | 6.8 | 3.8 | 3.8 | 4 |
| Freezing | before | after | | | |
| O.D. | 0.241 | 0.295 | | | |
| % of free propranolol | 4 | 4.8 | | | |
| Lyophilization | before | after | | | |
| O.D. | 0.241 | 0.247 | | | |
| % of free propranolol | 4 | 4.1 | | | |
| Atomization | before | after | | | |
| O.D. | 0.24 | 0.11 | | | |
| % of free propranolol | 4 | 1.9 | | | |

In all cases, the degree of leakage is very low and even decreases with atomization.

EXAMPLE 18

Study of the Pharmacokinetics of Encapsulated Antibiotics

In order to evaluate the influence of the encapsulation on the pharmacokinetics of two antibiotics, butirosin according to Example 6 and erythromycin according to Example 13, we carried out the determination in plasma as a function of time for these two antibiotics after administration in the free form and in the encapsulated form.

Experimental procedure

The injections are given subcutaneously and intravenously to male rabbits of the "White New Zealand" type weighing approximately 3 kg. The samples are taken at the lateral vein of the ear in amounts of 200 µl of blood/sample. The blood is immediately centrifuged at 8000 rpm for 15 min. The serum is withdrawn and stored at 4° C. until used.

Method of determination

Butirosin, like erythromycin, is determined by measuring the lysis zones (agar cylinders method) in an agar medium (bioMérieux) inoculated with 1000 cfu/ml of *Bacillus subtilis* and incubated at 37° C. for 18 hours. The bioMérieux agar medium consists of 6 g of bio-Gelytone, 3 g of yeast extract, 1.5 g of beef extract and 15 g of agar per 1 l of distilled water. The pH of the medium is adjusted to 9.

Procedure

The serum samples are deposited in the wells made in the agar medium (30 µl/well). Reference solutions representing known amounts of antibiotic are also deposited in the dish.

BUTIROSIN

| µg/ml standard range | 0.5 | 1  | 2  | 5  | 10 | 20 | 50 |
|----------------------|-----|----|----|----|----|----|----|
| Diameter (mm)        | 14  | 17 | 19 | 22 | 24 | 26 | 28 |

Subcutaneous injection

The amounts injected are 1 ml containing 9 mg of butirosin in the free or encapsulated form.

| Time | 30 min | 1 h | 2 h | 4 h | 6 h | 12 h | 18 h |
|------|--------|-----|-----|-----|-----|------|------|
| Free φ mm | 24 | 23 | 22 | 18 | 13 | 0 | 0 |
| butirosin µg/ml | 9 | 7 | 5 | 2 | 0.1 | 0 | 0 |
| Encapsulated φ mm | 0 | 0 | 0 | 16 | 16 | 14 | 15 |
| butirosin µg/ml | 0 | 0 | 0 | 0.8 | 0.8 | 0.5 | 0.6 |
| BVSM alone µg/ml | 0 | 0 | 0 | 0 | 0 | 0 | 0 |

It is found that free butirosin diffuses very rapidly in the plasma and is eliminated after 6 hours. In contrast, the encapsulated butirosin appeared in the circulation very much later (4h) and maintains a low but significant level.

Intravenous injection 4 ml of a physiological solution containing 5 mg of butirosin either in the free form or encapsulated in 100 mg of BVSM are injected. The solution is prepared from 8 g/l NaCl, 0.2 g/l KCl, 0.1 g/l anhydrous CaC$_{12}$ (sic), 0.1 g/l MgCl$_2$, 3.18 g/l Na$_2$HPO$_4$ and 0.2 g/l KH$_2$PO$_4$, adjusted to pH 7.4.

The injections are made slowly in the external vein of the ear after vasodilatation with warm water and disinfection with ethanol at 70° C.

| Time | ½ h | 1 h | 2 h | 3 h | 24 h |
|------|-----|-----|-----|-----|------|
| Inhibition diameter (mm) | 24.3 | 23 | 19 | 17 | 0 |
| Free butirosin µg/ml | 11 | 7 | 2 | 1 | 0 |

| Time | ½ h | 1 h | 2 h | 3 h | 24 h |
|------|-----|-----|-----|-----|------|
| Inhibition diameter (mm) | 19 | 17 | 17 | 17 | 17 |
| Encapsulated butirosin µg/ml | 2 | 1 | 1 | 1 | 1 |

It is noted that the free butirosin diffuses very rapidly into the plasma and is also eliminated very rapidly. The encapsulated butirosin also starts to diffuse very rapidly but at a much lower rate which is maintained over time.

It would therefore appear that metabolism of the BVSM leads to the liberation of butirosin which is more rapid in the case of IV injection than with subcutaneous injection. The liberation of the antibiotic in these two cases is controlled and stabilized by the encapsulation in the BVSM.

ERYTHROMYCIN

The amounts injected are 1 ml containing 15 mg of free or encapsulated erythromycin. For reasons of solubility, free erythromycin is dissolved in a water/ethanol (85:15) mixture.

| µg/ml standard range | 10 | 25 | 100 | 250 | 1,000 | |
|----------------------|----|----|-----|-----|-------|---|
| Diameter (mm) | 26 | 29 | 31 | 33 | 37 | |
| Time | 1 h | 3 h | 6 h | 9 h | 12 h | 24 h |
| Free φ mm | 37 | 35 | 28 | 27 | 26 | |
| erythromycin µg/ml | | 1,000 | 500 | 25 | 15 | 10 |
| Encapsulated φ mm | 0 | 32 | 27 | 26 | 26 | 26 |
| erythromycin µg/ml | 0 | 250 | 15 | 10 | 10 | 10 |
| BVSM alone φ mm | 0 | 0 | 0 | 0 | 0 | 0 |
| µg/ml | 0 | 0 | 0 | 0 | 0 | 0 |

It is found that erythromycin diffuses relatively slowly in the plasma. The free form enables a higher initial level to be achieved in the plasma than the encapsulated form. At the end of 24 hours a difference is no longer observed between the two forms.

EXAMPLE 19

Study of the Enzymatic Activity of Peroxidase Anchored to the Surface of the BVSM The enzymatic activity is measured by the ortho-phenylenediamine method.

Procedure

Two solutions of reactants are prepared.
Solution A: 0.012% (V/V) hydrogen peroxide solution of commercial 33% hydrogen peroxide solution in a citrate buffer (citric acid/sodium dihydrogen phosphate) at pH 5.
Solution B: 0.04% (Wt/V) solution of ortho-phenylenediamine in the citrate buffer.
The following are poured in sequence into 5 ml tubes: the peroxidase standard or peroxidase to be determined as a solution in 500 µl of citrate buffer,
500 µl of solution A,
500 µl of solution B.
The mixtures are agitated with a vortex mixer. The mixtures are incubated for 30 min at room temperature and the optical density at 492 nm is measured against the buffer.

| | Standard series | | | | |
|---|---|---|---|---|---|
| Standard (µg/ml) | 0.5 | 1 | 1.5 | 2 | 2.5 |

-continued

| Standard series | | | | | |
|---|---|---|---|---|---|
| O.D. (492 nm) | 0.135 | 0.380 | 0.405 | 0.550 | 0.675 |

Determination of the enzymatic activity of peroxidase immobilized on the BVSM.

The BVSM containing peroxidase are centrifuged, washed and resuspended in water. An aliquot is taken which is diluted 10,000 times and 500 μl of this diluted aliquot is taken for the enzymatic test.

| Sample | Neutral BVSM | | | Acid BVSM | | |
|---|---|---|---|---|---|---|
| | N1 | N2 | N3 | A1 | A2 | A3 |
| Concentration of bound enzyme (μg/ml) | 2.00 | 2.00 | 2.00 | 2.00 | 2.00 | 2.00 |
| O.D. (492 nm) | 0.391 | 0.387 | 0.393 | 0.555 | 0.542 | 0.553 |
| Average O.D. | | 0.390 | | | 0.550 | |
| Equivalent of free enzyme | | 1.200 μg/ml | | | 2.00 μg/ml | |
| % activity immobilized enzyme/ free enzyme | | 60 | | | 100 | |

It would therefore appear that the enzymatic activity of the peroxidase anchored to the surface of the BVSM depends to a large degree on the structure of the BVSM itself. Taking into account the lowering of the reaction kinetics which is inevitably associated with the anchoring of the peroxidase, the results obtained with the acid BVSM are particularly advantageous.

We claim:

1. Particulate carrier, characterized in that it comprises:
   a hydrophilic, non-liquid core, said core having an average size of between 10 nm and 5 μm;
   a first layer or ring of lipid nature bonded to the core by covalent bonds;
   a second layer or outer shell of amphiphilic compounds bonded to the first lipid layer by hydrophobic interactions.

2. Carrier according to claim 1, characterized in that the hydrophilic core consists of a crosslinked hydrophilic polymer.

3. Carrier according to claim 2, characterized in that the crosslinked hydrophilic polymer is a crosslinked polysaccharide.

4. Carrier according to claim 3, characterized in that the polysaccharide is chosen from: dextran, starch and cellulose and their derivatives.

5. Carrier according to claim 3, characterized in that the polysaccharide derivative carries acid or basic ionic charges distributed in a homogeneous manner in the volume of the core.

6. Carrier according to claim 5, characterized in that the polysaccharide derivative is obtained by reaction of a compound capable of forming a covalent bond with the OH function of the polysaccharide and also carries a positive or negative ionic fraction.

7. Carrier according to claim 5, characterized in that the compound is succinic acid or its derivatives.

8. Carrier according to claim 1, characterized in that the core has an average size of between 20 and 70 nm.

9. Carrier according to claim 1, characterized in that the first layer consists of a compound chosen from: sterols, fatty acids, fatty amines, phospholipids, hydrophobic amino acids and alkoxy ethers, and their mixtures.

10. Carrier according to claim 1, characterized in that the lipid layer is chemically coupled to the core by the hydroxyl functions or the functions derived from the hydroxyl functions of the said cores.

11. Carrier according to claim 1, characterized in that the second layer consists of a phospholipid or of a surfactant.

12. Carrier according to claim 1, characterized in that it also comprises, in one of the layers or the core, a molecule having biological activity.

13. Carrier according to claim 1, characterized in that the molecule having a biological activity is chosen from:
   antibiotics and antiviral agents,
   proteins, proteoglycans and peptides,
   polysaccharides and lipopolysaccharides,
   antibodies,
   insecticides and fungicides,
   compounds acting on the cardiovascular system,
   anti-cancer agents,
   anti-malarial agents and
   anti-asthmatic agents.

14. Carrier according to claim 1, characterized in that the carrier is labeled.

15. Carrier according to claim 14, characterized in that the carrier is labeled radioactively.

16. Carrier according to claim 1, characterized in that it is sterilized.

17. Carrier according to claim 1, characterized in that it is in the lyophilized form or atomized with a lyophilization agent.

18. Carrier according to claim 17, characterized in that the lyophilization agent is a sugar.

19. Process for the preparation of a particulate carrier according to claim 1, comprising the following steps:
   preparing a core by crosslinking a hydrophilic polymer and producing particles of the order of 10 nm to 5 μm by ultrasonic fragmentation or high pressure extrusion.
   coupling lipid compounds to reactive functions at the surface of the core by reacting the core and a derivative of lipid compounds, in order to form the first layer, and
   introducing amphiphilic compounds in hydrophobic contact with the first layer in order to create the second layer.

20. Process according to claim 19, characterized in that step b) is carried out in an aprotic medium which is a non-solvent for polysaccharides.

21. Process according to claim 19, characterized in that step c) is conducted with the aid of a method for the preparation of liposomes.

22. Process according to claim 19, characterized in that a molecule having biological activity is introduced during one of the steps of the process or into the finished carrier.

23. Composition having biological activity, characterized in that it comprises a carrier according to claim 1.

24. A particulate vehicle according to claim 14, as a diagnostic agent.

* * * * *

UNITED STATES PATENT AND TRADEMARK OFFICE
CERTIFICATE OF CORRECTION

PATENT NO. : 5,151,264

DATED : September 29, 1992

INVENTOR(S) : Daniel SAMAIN, Jean-Louis BEC, Edith COHEN, Frederique NGUYEN, and Marianne PEYROT It is certified that error appears in the above-identified patent and that said Letters Patent is hereby corrected as shown below:

On the title page,
Item [73] Assignee, change "Centre National de la Recherch Scientifique" to --Centre National de la Recherche Scientifique (CNRS)--.

Signed and Sealed this

First Day of March, 1994

Attest:

BRUCE LEHMAN

*Attesting Officer*     *Commissioner of Patents and Trademarks*